United States Patent [19]

Sugiyama et al.

[11] Patent Number: 5,017,368

[45] Date of Patent: May 21, 1991

[54] COMPOSITION FOR APPLICATION TO HAIR OR SCALP

[75] Inventors: Keikichi Sugiyama, No. 18-13, Ishigamidai 1-chome, Oiso-machi, Naka-gun, Kanagawa-ken; Koji Takada; Akira Fukushima, both of Fujisawa; Makoto Egawa, Odawara, all of Japan

[73] Assignee: Keikichi Sugiyama, Kanagawa, Japan

[21] Appl. No.: 472,438

[22] Filed: Jan. 31, 1990

Related U.S. Application Data

[63] Continuation of Ser. No. 201,019, Jun. 1, 1988, abandoned.

[30] Foreign Application Priority Data

Jun. 1, 1987 [JP] Japan .................................. 62-137982
Jun. 3, 1987 [JP] Japan .................................. 62-139118

[51] Int. Cl.$^5$ ........................ A61K 7/06; A61K 31/35
[52] U.S. Cl. ........................................ 424/70; 424/74; 514/454; 514/455
[58] Field of Search ................... 424/70, 74; 514/454, 514/455

[56] References Cited

FOREIGN PATENT DOCUMENTS

| 1223212 | 6/1987 | Canada . |
| 1234355 | 3/1988 | Canada . |
| 0102534 | 3/1984 | European Pat. Off. . |
| 0129778 | 1/1985 | European Pat. Off. . |
| 59-27809 | 2/1984 | Japan . |
| 60-4113 | 1/1985 | Japan . |
| WO85/03637 | 8/1985 | PCT Int'l Appl. . |
| WO87/04623 | 8/1987 | PCT Int'l Appl. . |

OTHER PUBLICATIONS

PCT Publication No. WO-87/04623 publication date Aug. 13, 1987.
PCT Publication No. WO-85/03637 publication date Aug. 29, 1985.
J. Endocrinology, vol. 90, pp. 89–96, (1981).

Primary Examiner—John W. Rollins
Attorney, Agent, or Firm—Burns, Doane, Swecker & Mathis

[57] ABSTRACT

A composition for application to hair or scalp comprises (A) at least one compound selected from the group consisting of (i) forskolin and derivatives thereof and (ii) peptides having a basic skeletal structure represented by the following general formula (I):

-P-Glu-His-Q-Arg-Trp-Gly-Lys-      (I)

(wherein P represents an L-norleucine or L-methionine residue; Q represents a D- or L-phenylalamine residue; and Glu, His, Arg, Trp, Gly and Lys are L-glutamic acid, L-histidine, L-arginine, L-tryptophan, glycine and L-lysine residues respectively); or the component A and (B) at least one compound selected from the group consisting of aliphatic acids, alcohols and derivatives thereof having an odd number of carbon atoms. The composition for hair or scalp exhibits excellent effect of preventing graying of the hair and restoring grayed hair to its natural color upon externally applied to the scalp and is highly safe as regards to the possibility of causing skin damage. Therefore, the composition can be widely used in various forms capable of being externally applied to the scalp.

6 Claims, No Drawings

COMPOSITION FOR APPLICATION TO HAIR OR SCALP

This application is a continuation of application Ser. No. 07/201,019, filed June 1, 1988, now abandoned.

BACKGROUND OF THE INVENTION

1. Field of the Invention

The present invention relates to a composition for application to hair or scalp in the manner of a hair tonic, a hair cream or the like, which, upon application to the scalp, activates melanocytes of the radix pili and improves the melanin synthesis function thereof, thereby preventing graying of the hair and restoring grayed hair to its natural color.

2. Description of the Prior Art

Graying of the hair is a universal aging phenomenon. While hair dyes are commonly used to dye grayed hair, the use of such dyes is troublesome and sometimes causes side-effects such as a rash. Therefore, many users find hair eyes to be an unsatisfactory solution. There has thus been a great need for developing a pharmaceutical agent or a costmetic composition for hair capable of essentially preventing graying of the hair and restoring grayed hair to its natural color.

In accordance with such needs, for instance, Japanese Patent Un-examined Publication (hereunder referred to as "J.P. KOKAI") Nos. 60-174705, 61-165310, 62-45527, 62-63509 and 62-63510 propose some solutions therefor. However, the cosmetic compositions proposed therein are not practically acceptable because of the low stability of their active components and insufficient safety.

SUMMARY OF THE INVENTION

Many people are annoyed by their grayed hair and there is a great need for developing compositions for preventing graying of the hair or restoring grayed hair to its natural color without causing side-effects such as those mentioned above.

Accordingly, it is a principal object of the present invention to provide a composition for application to hair or scalp, which is capable of preventing graying of the hair or restoring grayed hair to its natural color upon application of the same to the scalp and which causes no side-effects and has high safety.

The inventors of the present invention have conducted various studies of methods for activating the melanocytes of the radix pili and thus have found that the aforementioned problems can effectively be eliminated by utilizing forskolin and derivatives thereof, which are known to activate the adenyl cylase system that plays an important role as an information transmission system in living organisms, and a specific peptide and derivatives thereof, and that the effect of preventing graying of the hair or restoring grayed hair to its natural color can be attained and the aforementioned problems can also be effectively solved by using the foregoing specific substances in combination with at least one specific substance having an odd number of carbon atoms, which is known to have excellent hair growth promoting effect as an effective component of hair growth agents (see J.P. KOKAI Nos. 59-27809 and 60-4113). The present invention has been completed on the basis of the aforementioned new findings.

According to an aspect of the present invention, there is provided a composition for application to hair or scalp comprising (A) at least one compound selected from the group consisting of (i) forskolin and derivatives thereof;

(ii) peptides having a basic skeletal structure (or amino acid sequence) represented by the following general formula:

-P-Glu-His-Q-Arg-Trp-Gly-Lys- (I)

wherein P represents an L-norleucine or L-methionine residue; Q represents a D- or L-phenylalanine residue; and Glu, His, Arg, Trp, Gly and Lys represent L-glutamic acid, L-histidine, L-arginine, L-tryptophane, glycine and L-lysine residues respectively.

According to another aspect of the present invention, there is provided a composition for application to hair or scalp comprising: (A) at least one compound selected from the group consisting of (i) forskolin and derivatives thereof; and (ii) peptides having a basic skeletal structure represented by the general formula (I) defined above; and (B) at least one compound selected from the group consisting of aliphatic acids, alcohols and derivatives thereof having an odd number of carbon atoms.

DETAILED EXPLANATION OF THE INVENTION

In the composition of the present invention, any compounds may be used as the component (A) so far as they have, in the molecules, the skeletal structure represented by the forskolin and derivatives thereof or peptides represented by the general formula (I). However, it is preferable to use compounds represented by the following general formulae (II) (forskolin and derivatives thereof) or (III) (peptides and derivatives thereof):

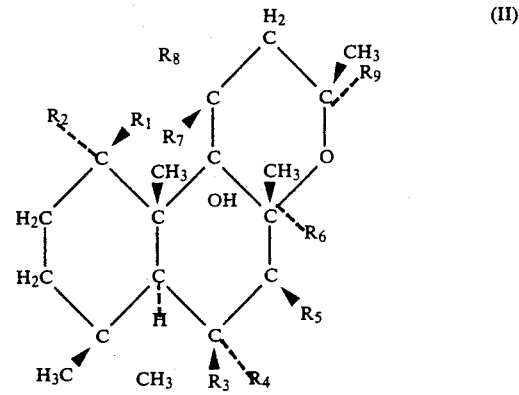

In the formula (II), $R_1$ to $R_8$ each represents a hydrogen atom, an oxygen atom, a hydroxyl group, an amino group, an -0-acyl group having 1 to 25, preferably 1 to 19 carbon atoms, an acyl group having 1 to 25, preferably 1 to 19 carbon atoms, an -0-alkyl group having 1 to 25, preferably 1 to 19 carbon atoms, an alkyl group having 1 to 25, preferably 1 to 19 carbon atoms, a diethylaminomethyl group or a toluenesulfonyl group, provided that if they represent oxygen atoms, they form double bonds together with the carbon atoms to which they are bonded. In this respect, if one of each pair of ($R_1$, $R_2$), ($R_3$, $R_4$), ($R_5$, $R_6$) or ($R_7$, $R_8$) is an oxygen atom, the compound is preferably that forming a double bond with the carbon atom without having other atoms or groups listed above as the other substituents of each pair. $R_7$ and $R_8$ are preferably oxygen atoms or $R_7$ is an hydroxyl group and $R_8$ is a hydrogen atom. $R_9$ represents a hydrogen atom, an alkenyl group having 2 to 25, preferably 2 to 19 carbon atoms, an alkyl group having 1 to 25, preferably 1 to 19 carbon atoms, a dialkylaminohydroxyethyl group having 1 to 25, preferably 1 to 19 carbon atoms, an aldehyde group or an epoxy group, provided that the acyl and alkyl groups may have substituents such as halogen atoms and may contain aromatic ring(s) and that the compounds may form a carbonate or sulfonate between $R_1$, $R_2$ and hydroxyl group at 9-position; $R_3$, $R_4$ and $R_5$, $R_6$.

X-P-Glu-His-Q-Arg-Trp-Gly-Lys-Y    (III)

In the formula (III), X represents an acetyl group, an amino acid residue or an acetyl derivative thereof, or a peptide residue having 2 to 10 amino acid residues or an acetyl derivative thereof, preferably an acetyl group or an acetyl derivative of an amino acid residue or a peptide residue. Y represents an amino group, an amino acid residue or an amide derivative thereof or a peptide residue having 2 to 5 amino acid residues or an amide derivative thereof, preferably an amino group of an amide derivative of an amino acid residue or a peptide residue and other symbols are the same as those described above.

The compounds represented by the formula (II) include, for instance forskolin (chemical name thereof 7-beta-acetoxy-8,13-epoxy-1-alpha,6-beta,9-alpha-trihydroxylabd 14-en-11-one; i.e.,the compound of the formula (II) in which $R_1$, $R_4$ and $R_6$ are hydrogen atoms, $R_2$ and $R_3$ are hydrodxyl groups, R5 is an acetoxy group, $R_7$ and $R_8$ are an oxygen atom to form carbonyl together with the carbon atom to which they are bonded and Rg is a vinyl group), specific derivatives and salts thereof. The forskolin used in the invention is a substance which is isolated from extracts of roots of Perilla plants such as Coleus forskohlii and purified, whereafter the structural formula is determined. The compounds have recently attracted attention because of their excellent physiological effects such as hypotensive action and muscle contractile force enforcing action. The compounds may also be synthesized from their intermediates. .These compound-s have already been put on the magnet as biochemical agents.

In the present invention, it is possible to use a crude extract obtained by extracting the roots of plants such as Coleus forkohlii, containing forskolin related compounds, with a solvent such as methanol, those obtained by further separating and purifying the crude extract by, for instance, chromatography technique, those synthesized from intermediates thereof and derivatives thereof obtained by a synthetic method.

Specific examples thereof are forskolin, 14,15-dihydroforskolin, 11-beta-hydroxylforskolin, 1,6-diacetylforskolin,, 7-deacetylforskolin, 6-acetyl-7-deacetylforskolin, 7-succinyl-7-deacetylforskolin, 7-butyryl-7-deacetylforskolin, 7-toluenesulfonyl-7-deacetylforskolin, 6-hexanoylforskolin, 1-diethylaminomethyl-6-acetyl-7-deacetylforskolin, forskolin 1,9-carbonate, forskolin 1,9-sulfonate, forskolin 6,7-carbonate and forskolin 1,9; 6,7-dicarbonate, which may be used alone or in combination. Among the foregoing forskolin related compounds, particularly preferred is forskolin.

The compounds represented by the formula (III) as used herein are, for instance, melanocyte-stimulating hormone (which is also called melanotropin and referred to as "MSH" below) and fragments and derivatives thereof. Specific examples thereof are alpha-MSH (N-acetyl-Ser-Tyr-Ser-Met-Glu-His-Phe-Arg-Trp-Gly-Lys-Pro-Val-NH$_2$) and the derivative thereof, i.e., desacetyl alpha-MSH (Des-Ac-alpha-MSH), diacetyl-alpha-MSH ((Di-Ac)-alpha-MSH), (Val-OH13)-alpha-MSH, (Nle$^4$, D-Phe$^7$)-alpha-MSH, (Nle$^4$)-alpha-MSH, (D-Phe$^7$)-alpha-MSH, human beta-MSH (Ala-Glu-Lys-Lys-Asp-Glu-Gly-Pro-Tyr-Arg-Met-Glu-His-Phe-Arg-Trp-Gly-Ser-Pro-Pro-Lys-Asp), hog beta-MSH (Asp-Glu-Gly-Pro-Tyr-Lys-Met-Glu-His-Phe-Arg-Trp-Gly-Ser-Pro-Pro-Lys-Asp) and bovine beta-MSH (having the same amino acid sequence as that of the hog bet-MSH in which Ser is substituted for Glu at 2-position).

In the foregoing structural formula, the amino acid residues constituting peptides are expressed by the conventional 3-character abbreviation (hereunder the same unless otherwise specified).

The compounds represented by the foregoing general formula (III) may be in the form of those which are extracted from the organs or tissues of animals such as hog and bovine or further purified; those synthesized and further chemically modified; and salts thereof. Examples thereof include a 4-11 fragment of alpha-MSH of which amino acid residues at 4- and 7-positions have substituents, namely N-acetyl-Nle-Glu-His-D-Phe-Arg-Trp-Gly-Lys-NH$_2$.

Particularly preferred examples of the compounds represented by the formula (III) are (Nle$^4$, D-Phe$^7$)-alpha-MSH, (Nle$^4$)-alpha-MSH, (D-Phe$^7$)-alpha-MSH and N-acetyl-Nle-Glu-His-D-Phe-Arg-Trp-Gly-Lys-NH$_2$.

In the present invention, the component (A) may be used alone or in combination or further in combination with the components (B) detailed below and the resultant composition is directly applied to the scalp thereby providing a greatly improved effect of preventing graying of the hair and restoring grayed hair to that of natural color. In such a composition for application to hair or scalp, the compounds (A) may be used in any amount. However, they are generally used in the order of 0.000001 to 10% by weight (hereinafter referred to as "%" for simplicity), preferably 0.00001 to 5%. Particularly, compounds (i) are used in an amount of 0.01 to 5% and compounds (ii) 0.00001 to 0.1%.

The fatty (or aliphatic) acid moiety of the fatty acids and the derivatives thereof having an odd number of carbon atoms used as component (B) may be unsaturated or saturated one so far as the number of carbon atoms (chain length) constituting the carbon chain thereof is an odd number. In this connection, the unsaturated fatty acids may include a plurality of double bonds therein. Examples of such fatty acids include lower fatty acids such as propionic acid (carbon chain length 3) and valeric acid (carbon chain length =5); and higher fatty acids such as pentadecanoic acid (carbon chain length 15) and heptadecanoic acid (carbon chain length =17). Preferred are those having carbon atoms of 3 to 25, more preferably 9 to 19.

The composition for hair of the present invention may include any derivatives of these fatty acids having an odd number of carbon atoms provided that they exert no influence on human bodies. Preferred examples of such derivatives of fatty acids are as follows:

(a) Monoglycerides represented by the following general formulas (IV) and (V):

$$\begin{array}{ll}\text{CH}_2\text{OCOR}_{10} & \text{CH}_2(\text{OH}) \\ | & | \\ \text{CH(OH)} \quad \text{(IV)} & \text{CHOCOR}_{10} \quad \text{(V)} \\ | & | \\ \text{CH}_2(\text{OH}) & \text{CH}_2(\text{OH})\end{array}$$

wherein $R_{10}$ represents a linear organic group having an even number of carbon atoms;

(b) Diglycerides represented by the following general formulas (VI) and (VII):

$$\begin{array}{ll}\text{CH}_2\text{OCOR}_{11} & \text{CH}_2\text{OCOR}_{11} \\ | & | \\ \text{CHOCOR}_{12} \quad \text{(VI)} & \text{CH(OH)} \quad \text{(VII)} \\ | & | \\ \text{CH}_2(\text{OH}) & \text{CH}_2\text{OCOR}_{12}\end{array}$$

wherein $R_{11}$ and $R_{12}$ each represents a chain organic group with the proviso that at least one of them is a linear organic group having an even number of carbon atoms;

(c) Triglycerides represented by the following general formula (VIII):

$$\begin{array}{ll}\text{CH}_2\text{OCOR}_{11} & \text{(VIII)} \\ | & \\ \text{CHOCOR}_{12} & \\ | & \\ \text{CH}_2\text{OCOR}_{13} & \end{array}$$

wherein $R_{11}$ and $R_{13}$ each represents a chain organic group with the proviso that at least one of them is a linear organic group having an even number of carbon atoms;

(d) Fatty acid salts represented by the following general formula (IX):

$$(R_{10}\text{COO})_n M \quad \text{(IX)}$$

wherein $R_{10}$ is the same as defined above, M represents a metal atom and n is an integer corresponding to the valency of M;

(e) Esters represented by the following general formula (X):

$$R_{10}\text{COOR}_{14} \quad \text{(X)}$$

wherein $R_{10}$ is the same as defined above and $R_{14}$ represents a monovalent or a bivalent alcohol residue, an amine residue, a polyoxyethylene residue, a sorbitan residue or a sucrose residue;

(f) Primary amides represented by the following general formula (XI):

$$R_{10}\text{CONR}_{15}R_{16} \quad \text{(XI)}$$

wherein $R_{10}$ is the same as defined above and $R_{15}$ and $R_{16}$ each represents a hydrogen atom or an organic group;

(g) Secondary amides represented by the following general formula (XII):

$$R_{11}\text{CON}(R_{15})\text{COR}_{12} \quad \text{(XII)}$$

wherein $R_{11}$ and $R_{12}$ are the same as those defined above in connection with compounds (VI) or (VII) and $R_{15}$ is the same as defined above;

(h) Tertiary amides represented by the following general formula (XIII):

$$R_{11}\text{CON}(\text{COR}_{13})\text{COR}_{12} \quad \text{(XIII)}$$

wherein $R_{11}$ to $R_{13}$ are the same as those defined above;

(i) Dibasic acids and salts thereof represented by the following general formula (XIV):

$$\text{HOOCR}_{17}\text{COOH} \quad \text{(XIV)}$$

wherein $R_{17}$ is a linear organic group having an odd number of carbon atoms;

(j) Sterol esters represented by the following general formula (XV):

[Structure (XV): sterol with $R_{10}\text{COO}$— substituent]

wherein $R_{10}$ is the same as defined above;

(k) Phospholipids represented by the following general formula (XVI):

$$\begin{array}{l}\text{CH}_2\text{OCOR}_{11} \\ | \\ \text{CHOCOR}_{12} \\ | \\ \text{H}_2\text{C}-\text{O}\diagdown \quad \diagup\text{O}^- \\ \qquad \qquad \text{P} \\ \qquad \diagup \quad \diagdown \\ \text{O} \qquad \text{O}-\text{X}_1\end{array} \quad \text{(XVI)}$$

wherein $R_{11}$ and $R_{12}$ are the same as defined above and $X_1$ represents a choline residue, an ethanolamine residue, a serine residue or an inositol residue;

(l) Phosphatidic acids represented by the following general formula (XVII):

$$\begin{array}{l}\text{CH}_2\text{OCOR}_{11} \\ | \\ \text{CHOCOR}_{12} \\ | \\ \text{H}_2\text{C}-\text{O}\diagdown \quad \diagup\text{O}^- \\ \qquad \qquad \text{P} \\ \qquad \diagup \quad \diagdown \\ \text{O} \qquad \text{O}^-\end{array} \quad \text{(XVII)}$$

wherein $R_{11}$ and $R_{12}$ are the same as defined above; and (m) Sphingolipids represented by the following general formula (XVIII):

$$\begin{array}{l}\text{CH}_3(\text{CH}_2)_{12}\text{CH}=\text{CH}-\text{CH}-\text{CH}-\text{CH}_2-\text{O}-\text{X}_2 \\ \qquad \qquad \qquad \qquad \qquad | \qquad | \\ \qquad \qquad \qquad \qquad \qquad \text{OH} \quad \text{NH} \\ \qquad \qquad \qquad \qquad \qquad \qquad \quad | \\ \qquad \qquad \qquad \qquad \qquad \qquad \quad \text{C}=\text{O} \\ \qquad \qquad \qquad \qquad \qquad \qquad \quad | \\ \qquad \qquad \qquad \qquad \qquad \qquad \quad R_{10}\end{array} \quad \text{(XVIII)}$$

wherein $R_{10}$ is the same as defined above and $X_2$ is a sugar residue, a phosphate residue or an amine base residue.

In the above general formulas, $R_{10}$ is preferably the linear organic group having 2 to 24, more preferably 8 to 18 carbon atoms. At least one of $R_{11}$ and $R_{12}$ in the formulas (VI), (VII), (XVI) and (XVII) is the chain organic group having an even number of carbon atoms (preferably 2 to 24 and more preferably 8 to 18) and it is particularly preferred that both of them represent those having an even number of carbon atoms.

At least one of $R_{11}$ to $R_{13}$ in the formulas (VIII) and (XIII) is the chain organic group having carbon atoms of even number, preferably 2 to 24, more preferably 8 to 18 and it is particularly preferred that all the substituents $R_{11}$ and $R_{13}$ are those having an even number of carbon atoms falling within the foregoing range.

In the definition of $R_{14}$ of the formula (X), examples of the monovalent alcohol residue include those having 1 to 18 carbon atoms such as methanol and ethanol residues and examples of the amine residues include mono-, di- and triethanolamines. 20 As the organic groups represented by $R_{15}$ and $R_{16}$ in the formulas (XI) and (XII), alkyl groups having 1 to 18 carbon atoms such as methyl and ethyl groups are preferred. Preferred examples of $R_{17}$ in the formula (XIV) include hydrocarbon residues having 1 to 23 carbon atoms (more preferably 1 to 17) such as methylene group.

In the formula (XVI), if $X_1$ is a choline residue, the compound is phosphatidyl choline; if it is an ethanolamine residue, compound (XVI) is phosphatidyl ethanolamine; if it is a serine residue, the compound is phosphatidyl serine; and if it represents an inositol residue, the compound is phosphatidyl inositol. Moreover, examples of M in the formula (IX) include an alkali metal such as sodium, potassium, and lithium.

In the composition of the present invention, the components (B) listed above may be incorporated thereinto alone or in combination and specific examples thereof are fatty acids such as nonanoic acid, tridecanoic acid and pentadecanoic acid; monoglycerides such as glyceryl monotridecanoate, glyceryl monopentadecanoate and glyceryl monoheptadecanoate; diglycerides such as glyceryl diundecanoate, glyceryl ditridecanoate and glyceryl dipentadecanoate; triglycerides such as glyceryl trinonanoate, glyceryl tritridecanoate, glyceryl tripentadecanoate and diacetyl glyceryl monopentadecanoate; fatty acid salts such as potassium nonanoate and sodium pentadecanoate; esters such as ethyl pentadecanoate and methyl nonadecanoate; primary amides such as pentadecanoyl amide; secondary amides such as N-acetylpentadecanoyl amide; tertiary amides such as N,N-diacetylpentadecanoyl amide; dibasic acids and the salts thereof such as 1,13-tridecamethylenedicarboxylic acid; sterol esters such as choresterol pentadecanoate; phospholipids such as 1,2-dipentadecanoyl-glycero-3-phosphorylcholine; phosphatidic acids such as 1,2-dipentadecanoyl-glycero-3-phosphoric acid; and sphingolipids such as N-pentadecanoylsphingosine-1-phosphorylethanolamine.

The alcohols usable in the invention a component (B) may be saturated or unsaturated ones with the proviso that the number of carbon atoms constituting the carbon chain thereof is an odd number. Such unsaturated alcohols may include a plurality of double bonds therein. Examples thereof include lower alcohols such as propyl alcohol (chain length =3) and amyl alcohol (chain length 5) and higher alcohols such as tricosyl alcohol (chain length 23) and pentacosyl alcohol (chain length =25). In addition, the hydroxyl group may be bonded to any carbon atom of the carbon chain. Among these, preferred are those having 3 to 25 (more preferably 9 to 19) carbon atoms.

The derivatives of the alcohols listed above may be used herein and typical examples thereof are esters and ethers of the alcohols having an odd number of carbon atoms.

Such an ester is represented by the following general formula:

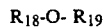

wherein $R_{18}$ represents an alcohol residue having an odd number (preferably 3 to 25 and more preferably 9 to 19) of carbon atoms and $R_{19}$ is a residue of organic acid such as an aliphatic acid residue (preferably having 2 to 24 carbon atoms), succinic acid, citric acid, foralic acid, lactic acid, pyruvic acid, malic acid and oxaloacetic acid; and residues of inorganic acids such as phosphoric acid.

Examples of such ethers as used herein are represented by the following general formula:

wherein $R_{18}$ is the same as that defined above and $R_{20}$ represents a monovalent alcohol residue (preferably having 2 to 24 carbon atoms); a residue of polyvalent alcohol such as glycerin, polyglycerin, ethylene glycol, propylene glycol and butanediol; or a residue of sugar such as dextrose, ribose, galactose, arabinose, mannose, xylose, sorbitol and mannitol. These ethers may have two or more of alcohol residues having an odd number of carbon atoms such as di- or tri-alkoxide (having an odd number of carbon atoms) of glycerin in a molecule.

The only requirement for the alcohol derivatives having an odd number of carbon atoms as used herein is to have alcohol residue(s) having an odd number of carbon atoms. Therefore, the acid residues in the aforementioned esters may be substituted with a variety of substituents and likewise the alcohol residues other than the former and the sugar residues of the ethers may be substituted with various substituents. In this respect, it is a matter of course that these residues and the substituents therefor should not exert any influence on human bodies.

Specific examples of these alcohols or derivatives thereof include undecyl alcohol, tridecyl alcohol, pentadecyl alcohol, heptadecyl alcohol, nonyl acetate, undecyl succinate, pentadecyl citrate, triundecyl glyceryl ether, and tripentadecyl glyceryl ether and they may be used alone or in combination.

The component (B) may be incorporated into the composition for hair of the present invention in any amount. The amount thereof in general varies dependent upon forms of the final products, the frequency of application thereof and the like, but, the component (B) may be used, in various compositions for hair or scalp, in an amount of about 0.01 to 20%, preferably 0.1 to 10%. In addition, the weight ratio of the component (A) to the component (B) is preferably 1/500,000 to 50/1.

In addition to the foregoing components, the composition of this invention may further comprise other pharmaceutical components such vitamins as vitamin A, vitamin $B_6$, vitamin E, pantothenic acid and biotin; such amino acids as methionine, cysteine, cystine and tyrosine; such antibacterial agents as salicylic acid, hinokitiol, resorcin and trichlorocarbanilide; and such hormones as ethynylestradiol and progesterone and these pharmaceutical components are preferably added to the compositions for hair or scalp in an amount of 0.0001 to 1%.

Moreover, other materials commonly used in preparations for hair can also be added to the composition for hair or scalp of the present invention and examples thereof are oils, water, surfactants, humectants, lower alcohols, thickening agents, antioxidants, chelating agents, pH adjusting agents, preservatives, perfumes and color additives. Examples of such oils include fats and oils such as olive oil, jojoba oil and hardened oil; waxes such as spermaceti, beeswax and lanolin; hydrocarbons such as liquid paraffin, ceresin and squalane, fatty acids such as stearic acid and oleic acid; alcohols such as cetanol, stearyl alcohol, lanolin alcohol and hexyl decanol; and esters such as isopropyl myristate and butyl stearate. These oils are incorporated into the composition for hair or scalp alone or in combination and the amount thereof ranges from 0.5 to 85%.

Examples of the surfactants are anionic surfactants such as sodium stearate, sodium cetylsulfate, polyoxyethylene lauryl ether phosphate and sodium N-acyl glutamate; cationic surfactants such as stearyldimethylbenzylammonium chloride and stearyltrimethylammonium chloride; amphoteric surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleyl ether, polyethylene glycol monostearate, polyoxyethylene sorbitan monopalmitate, polyoxyethylene coconut fatty acid monoethanolamide, polyoxyethylene polyoxypropylene glycol, polyoxyethylene castor oil and polyoxyethylene lanolin. These surfactants may be used in the composition for hair or scalp alone or in combination and the amount thereof falls within the range of 0.1 to 10%.

Moreover, there may be mentioned such humectants as glycerin, 1,3-butylene glycol and propylene glycol; such lower alcohols as ethanol and isopropanol; such thickening agents as polyethylene glycol and sodium carboxymethylcellulose; such antioxidants as dibutylhydroxytoluene, butylhydroxyanisole and propyl gallate; such chelating agents as disodium edetate and ethanehydroxy diphosphate; such pH adjusting agents as citric acid sodium citrate, boric acid, borax and disodium hydrogen phosphate; and such preservatives as methyl p-hydroxybenzoate, ethyl p-hydroxybenzoate, dehydroacetic acid, salicylic acid and benzoic acid.

In this respect, these optional components are not restricted to those specific examples listed above.

The compositions for hair or scalp of the present invention may be prepared by appropriately admixing the foregoing essential components and optional components and may be used in any forms capable of external use such as hair tonics, creams, lotions, milky lotions and ointments.

For instance, hair tonics comprise 0.00001 to 5% of the aforementioned essential components (A), 0.1 to 10% of the components (B), 15 to 99.5% of lower alcohols, 0 to 3% of the foregoing pharmaceutical components, 0 to 15% of the humectants, 0 to 85% of purified water, and up to small amounts of the perfumes and the color additives; hair creams comprise 0.00001 to 5% of the aforementioned essential components (A), 0.1 to 10% of the components (B), 20 to 80% of oil components, 0.5 to 15% of the surfactants, 0 to 15% of the humectants, 15 to 80% of purified water, and up to small amounts of the preservatives, antioxidants and the perfumes; and milky lotions comprise 0.00001 to 5% of the aforementioned essential components (A), 0.1 to 10% of the components (B), 5 to 30% of oil components, 0.5 to 15% of the surfactants, 0 to 15% of the humectants, 50 to 95% of purified water, and up to small amounts of the preservatives and the perfumes.

Although, the reason why the component (A) used in the composition of this invention exhibits such an excellent effect of preventing graying of the hair and restoring grayed hair to its natural color has not yet been clearly evidenced, it is assumed that, when externally applied, it penetrates into the melanocytes present in the scalp radix pili, and activates metanocytes to promote the synthesis of melanin and thereby how such excellent effect of preventing graying of the hair and restoring grayed hair to its natural color. Moreover, if the components (A) and (B) are used in combination, a synergistic effect may be expected, i.e., the effect of promoting the synthesis of melanin due to the component (A) and that of promoting the keratinization due to the component (B) synergistically promote the uptake of the resultant melanin granules by mother cells of the hair and, therefore, particularly excellent effect of preventing graying of the hair and restoring grayed hair to its natural color is provided. However, the detail of the effects of these components have been under investigation.

The aforementioned components (A), in particular forskolin related compounds are derived from Coleus forskohlii (Perilla plant) cultivated in the tropics for pickles and are composed of amino acids naturally present in the living bodies. Therefore, they are considered to be highly safe. When the level of safety was checked in order to make sure, no practical problem was observed with respect to skin irritation or skin sensitization and thus a high level of safety was confirmed. Likewise, when the components (A) and (B) were used in combination, no practical problems regarding safety were observed.

In accordance with the present invention, a composition for hair or scalp capable of preventing graying of the hair and restoring grayed hair to its natural color upon externally applied to the scalp is provided. Besides the composition is highly safe as regards the possibility of causing skin damages.

Therefore, the composition according to the present invention can be widely used in various forms capable of being externally applied to the scalp. Such forms include, for instance, cosmetic compositions such as hair tonics, creams, lotions, milky lotions, hair treatments, hair conditioners and ointments.

Furthermore, if the components (A) and (B) are simultaneously incorporated into the compositions of the present invention, the foregoing effects can further be enhanced.

The present invention will hereunder be explained in more detail with reference to the following non-limitative working examples. Moreover, the effects practically achieved by the composition of the present invention will also be discussed with reference to the following Comparative Examples.

EXAMPLE 1

It has been known that stress may cause graying of the hair. Then, animals were subjected to stress to deactivate the melanocytes thereof, thereby graying the hair thereof and investigation was conducted to determine how the composition for hair or scalp in which effective components of the invention had been incorporated could be effectively used to suppress the generation of grayed hair under such conditions.

Test Samples (hair tonics) having the compositions shown in Table I below, which comprise 0.001 to 0.05% of the component (A) and 2% of the component (B), were prepared. In Table I, the numerical values indicate the amount of each component added, which is expressed in % by weight (those in the following Tables are also shown in the same way). After hair had been removed from the back of each mouse in a group composed of 10 black mice, the foregoing hair tonics were repeatedly applied to the hair-free area of the mice in an amount of 0.1 ml each, twice a day for one month while intermittently stressing the animals. Thereafter, the regenerated hair of the animals per constant area was collected to determine the rate (%) of the grayed hair with respect to the total number of hairs (hereunder referred to as "grayed hair rate") and the results were summarized in Table II.

The abbreviations given below are used in Table II (these in the following Tables are also shown in the same way).

Peptide I: (Nle$^4$, D-Phe$^7$)-alpha-MSH;
Peptide II: N-acetyl-Nle-Glu-His-D-Phe-Arg-Trp-Gly-Lys-NH$_2$;

TABLE I

| Component | Amount |
| --- | --- |
| Test material (component (A)) | 0.001 to 0.1 |
| Test material (component (B)) | 2.0 |
| Ethanol | 85.0 |
| Polyethylene glycol 200 | 2.0 |
| Purified water | balance |

TABLE II

| Group No. | Stress | Test Component (A) (amount) | Materials Component (B) (amount) | Grayed Hair rate (%) |
| --- | --- | --- | --- | --- |
| 1 | — | — | — | 5.6 |
| 2 | applied | — | — | 16.8 |
| 3 | " | forskolin (0.05%) | — | 6.5 |
| 4 | " | forskolin (0.05%) | glyceryl monopentadecanoate | 3.9 |
| 5 | " | Peptide I (0.001%) | — | 7.1 |
| 6 | " | Peptide I (0.001%) | pentadecyl alcohol | 4.1 |
| 7 | " | Peptide II (0.001%) | — | 7.0 |
| 8 | " | Peptide II (0.001%) | tridecyl succinate | 4.2 |

As seen from the results summarized in Table II, the grayed hair rate of the group Nos. 3, 5 and 7 to which the component (A) of the present invention was applied more clearly lowered when compared with that of the group No. 2 which was stressed without applying Test Material. Furthermore, the grayed hair rate was remarkably lowered if the component (A) and (B) were used in combination (see the group Nos. 4, 6 and 8).

Consequently, these results listed in Table II clearly show that the use of the component (A) optionally combined with the component (B) makes it possible to quite effectively prevent the deactivation of melanocytes or allows for the deactivated melanocytes to restore thereby preventing graying of the hair and restoring grayed hair to its natural color.

EXAMPLE 2

Components shown in Table III other than ethanol were in order uniformly dissolved in ethanol to form hair tonics (Sample Nos.S-I to S-III). The composition of each sample is shown in Table III.

TABLE III

| Component | Present Invention I | Invention II | Comp. Ex. III |
| --- | --- | --- | --- |
| Ethanol | 98.4 | 99.4 | 99.5 |
| Glycerin | 0.5 | 0.5 | 0.5 |
| Forskolin | 0.1 | 0.1 | — |
| Glyceryl monopentadecanoate | 1.0 | — | — |
| Color additive | small amount | small amount | small amount |
| Perfume | small amount | small amount | small amount |

Two groups each of which comprised 20 persons (50 to 60 years old; composed of men and women) were selected and the hair tonics (Sample Nos.S-I and S-II) were separately applied to the scalp of each person of one group in accordance with Half-Head technique wherein Sample Nos.S-I and S-II were separately applied to the right half and the left of the scalp, on the other hand Samples (S-II and S-III were likewise separately applied to each person of the other group in the same manner twice a day (in the morning and at night) for 3 months. Then, the effects of preventing graying of the hair and restoring grayed hair to its natural color were estimated by comparing the conditions of the portions observed before and after the application of Samples and the results obtained were listed in Tables IV and V.

TABLE IV

| This Inv. (S-II) is better | This Inv. (S-II) is somewhat better | Same | Comp. Ex. (S-III) is somewhat better | Comp. Ex. (S-III) is better |
| --- | --- | --- | --- | --- |
| 6 | 8 | 6 | 0 | 0 |

TABLE V

| This Inv. (S-I) is better | This Inv. (S-I) is somewhat better | Same | This Inv. (S-II) is somewhat better | This Inv. (S-II) is better |
| --- | --- | --- | --- | --- |
| 2 | 9 | 6 | 3 | 0 |

The results listed in Tables IV and V demonstrate that the hair tonic (S-II) of the present invention containing forskolin makes it possible to lower the grayed hair rate and exhibits remarkable effect of preventing graying of the hair and restoring grayed hair to its natural color compared with the comparative hair tonic (S-III) and that the hair tonic of the invention (S-I) containing both forskolin and glyceryl monopentadecanoate exhibits such effect more excellent than that of the hair tonic (S-II).

In addition, during and after the application of the hair tonics of the present invention for 3 months, no abnormality was observed in the condition of the scalp.

EXAMPLE 3

Milky lotions (C-I to C-III) for hair were prepared by separately dissolving components 1 to 6 and components 7 to 11 listed in Table VI while heating them to 80° C., admixing and emulsifying these two solutions, adding component 12 during cooling the resultant emulsion with uniformly stirring and the effects of preventing graying of the hair and restoring grayed hair to its natural color were examined in the same manner as in Example 2. The results obtained are summarized in Tables VII and VIII below.

TABLE VI

| Component | Present Invention I | Invention II | Comp. Ex. III |
|---|---|---|---|
| 1 Stearic acid | 2.5 | 2.5 | 2.5 |
| 2 Cetanol | 1.5 | 1.5 | 1.5 |
| 3 Vaseline | 5.0 | 5.0 | 5.0 |
| 4 Liquid paraffin | 10.0 | 10.0 | 10.0 |
| 5 Polyethylene glycol monooleate | 2.0 | 2.0 | 2.0 |
| 6 Undecyl succinate | 2.0 | — | — |
| 7 Extract from Coleus forskohlii (including 2.1% of forskolin) | 1.0 | 1.0 | — |
| 8 Polyethylene glycol 1500 | 3.0 | 3.0 | 3.0 |
| 9 Triethanolamine | 1.0 | 1.0 | 1.0 |
| 10 Preservative | small amount | small amount | small amount |
| 11 Purified water | 72.0 | 74.0 | 75.0 |
| 12 Perfume | small amount | small amount | small amount |

TABLE VII

| This Inv. (C-II) is better | This Inv. (C-II) is somewhat better | Same | Comp. Ex. (C-III) is somewhat better | Comp. Ex. (C-III) is better |
|---|---|---|---|---|
| 5 | 9 | 6 | 0 | 0 |

TABLE VIII

| This Inv. (C-I) is better | This Inv. (C-I) is somewhat better | Same | This Inv. (C-II) is somewhat better | This Inv. (C-II) is better |
|---|---|---|---|---|
| 3 | 8 | 7 | 2 | 0 |

The results listed in Tables VII and VIII demonstrate that the milky lotion (C-II) of the present invention including forskolin-containing extract from Coleus forskohlii makes it possible to lower the grayed hair rate and exhibits remarkable effect of preventing graying of the hair and restoring grayed hair to its natural color compared with the comparative milky lotion (C-III) and that the milky lotion of the invention (C-I) containing both the extract from Coleus forskohlii and undecyl succinate exhibits such effect more excellent than that of the milky lotion (C-II).

In addition, during and after the application of the milky lotion of the present invention for 3 months, no abnormality was observed in the condition of the scalp.

EXAMPLE 4

Procedures similar to those in Example 2 were repeated except for using, instead of glyceryl monopentadecanoate, nonanoic acid, glyceryl diundeconoate, diacetyl glyceryl monopentadecanoate, sodium nonadecanoate, methyl heptadecanoate, tridecanoyl amide, N-acetyl undecanoyl amide, N,N-diacetyl nonanoyl amide, 1,13-tridecamethylenedicarboylic acid, choresterol nonanoate, 1,2-diundecanoyl-glycero-3-phosphorylcholine, 1,2-dipentadecanoyl-glycero-3-phosphoric acid, N-tridecanoylsphingosine-1-phosphorylethanolamine or tripentadecyl glyceryl ether to prepare similar hair tonics and the properties thereof were examined thereby the same effect of preventing graying of the hair and restoring grayed hair to its natural color as in Example 2 were obtained.

EXAMPLE 5

Components shown in Table IX other than ethanol were in order uniformly dissolved in ethanol to form hair tonics (T-I) to T-III). Composition of each Sample was shown in Table IX.

TABLE IX

| Component | Present Invention I | Invention II | Comp. Ex. III |
|---|---|---|---|
| Ethanol | 70.0 | 70.0 | 70.0 |
| Glycerin | 2.0 | 2.0 | 2.0 |
| Castor oil | 1.0 | 1.0 | 1.0 |
| Alpha-MSH | 0.08 | 0.08 | — |
| Glyceryl monopentadecanoate | 1.0 | — | — |
| Color additive | small amount | small amount | small amount |
| Perfume | small amount | small amount | small amount |
| Purified water | 25.92 | 25.92 | 27.0 |

The properties of the foregoing hair tonics were determined in the same manner as in Example 2. The results obtained are listed in Tables X and XI.

TABLE X

| This Inv. (T-II) is better | This Inv. (T-II) is somewhat better | Same | Comp. Ex. (T-III) is somewhat better | Comp. Ex. (T-III) is better |
|---|---|---|---|---|
| 3 | 10 | 7 | 0 | 0 |

TABLE XI

| This Inv. (T-I) is better | This Inv. (T-I) is somewhat better | Same | This Inv. (T-II) is somewhat better | This Inv. (T-II) is better |
|---|---|---|---|---|
| 2 | 9 | 5 | 4 | 0 |

The results listed in Tables X and XI demonstrate that the hair tonic (T-II) of the present invention including alpha-MSH makes it possible to lower the grayed hair rate and exhibits remarkable effect of preventing graying of the hair and restoring grayed hair to its natural color compared with the comparative hair tonic (T-III) and that the hair tonic of the invention (T-I) containing both alpha-MSH and glyceryl monopentadecanoate exhibits such effect more excellent than that of the hair tonic (T-II).

In addition, during and after the application of the hair tonics of the present invention for 3 months, no abnormality was observed in the condition of the scalp.

EXAMPLE 6

Procedures similar to those in Example 5 were repeated except for using, instead of glyceryl monopentadecanoate, nonanoic acid, glyceryl diundecanoate, diacetyl glyceryl monopentadecanoate, sodium nonadecanoate, methyl heptadecanoate, tridecanoyl amide, N-acetyl undecanoyl amide, N,N-diacetyl nonanoyl amide, 1,13-tridecamethylenedicarboxylic acid, choresterol nonanoate, 1,2-diundecanoyl-glycero-3-phosphorylcholine, 1,2-dipentadecanyol-glycero-3-phosphoric acid, N-tridecanoylsphingosine-1-phosphorylethanolamine or tripentadecyl glyceryl ether to prepare similar hair tonics and the properties thereof were examined thereby the same effect of preventing graying of the hair and restoring grayed hair to its natural color as in Example 5 were obtained.

EXAMPLE 7

Hair creams (HC-I to HC-III) for hair were prepared by separately dissolving components 1 to 8 and components 9 to 11 listed in Table XII while heating them to 80° C., admixing and emulsifying these two solutions, adding component 12 during cooling the resultant emulsion with uniformly stirring. In Table XII, P represents the averaged molar number of added ethylene oxide.

TABLE XII

| Component | Present Invention I | Invention II | Comp. Ex. III |
|---|---|---|---|
| 1 Lanolin | 2.0 | 2.0 | 2.0 |
| 2 Glyceryl monostearate | 5.5 | 5.5 | 5.5 |
| 3 Polyoxyethylene (p = 20) sorbitan monostearate | 2.0 | 2.0 | 2.0 |
| 4 Beeswax | 8.0 | 8.0 | 8.0 |
| 5 Liquid paraffin | 25.0 | 25.0 | 25.0 |
| 6 Hardened oil | 23.0 | 23.0 | 23.0 |
| 7 14,15-Dihydroforskolin | 1.0 | 1.0 | — |
| 8 Dodecyl alcohol | 3.0 | — | — |
| 9 Ethyl p-hydroxybenzoate | small amount | small amount | small amount |
| 10 Borax | 0.5 | 0.5 | 0.5 |
| 11 Purified water | balance | balance | balance |
| 12 Perfume | small amount | small amount | small amount |

Likewise, the effects of preventing graying of the hair and restoring grayed hair to its natural color were examined in the same manner as in Example 2. The results obtained are summarized in Tables XIII and XIV below.

TABLE XIII

| This Inv. (HC-II) is better | This Inv. (HC-II) is somewhat better | Same | Comp. Ex. (HC-III) is somewhat better | Comp. Ex. (HC-III) is better |
|---|---|---|---|---|
| 7 | 8 | 5 | 0 | 0 |

TABLE XIV

| This Inv. (HC-I) is better | This Inv. (HC-I) is somewhat better | Same | This Inv. (HC-II) is somewhat better | This Inv. (HC-II) is better |
|---|---|---|---|---|
| 3 | 7 | 7 | 3 | 0 |

The results listed in Tables XIII and XIV demonstrate that the hair cream ((HC-II) of the present invention including 14,15-dihydroforskolin makes it possible to lower the grayed hair rate and exhibits remarkable effect of preventing graying of the hair and restoring grayed hair to its natural color compared with the comparative hair cream (HC-III) and that the hair cream of the invention (HC-I) containing both 14,15-dihydroforskolin and tridecyl alcohol exhibits such effect more excellent than that of the hair cream (HC-II).

In addition, during and after the application of the hair creams of the present invention for 3 months, no abnormality was observed in the condition of the scalp

EXAMPLE 8

Hair creams were prepared accordingly in the same manner as in Example 7 except for using, instead of 14,15-dihydroforskolin, 11-beta-hydroxyforskolin, 1,6-diacetylforskolin, 7-deacetylforskolin, 6-acetyl-7-deacetylforskolin, 7-succinyl-7-deacetylforskolin, 7-butyryl-7-deacetylforskolin, 7-toluenesulfonyl-7-deacetylforskolin, 6-hexanoylforskolin, 1-diethylaminomethyl-6-acetyl-7-deacetylforskolin, forskolin 1,9-carbonate, forskolin 1,9-sulfonate, forskolin 6,7-carbonate or forskolin 1,9; 6,7-dicarbonate and the properties thereof were examined as in Example 7. As a result, the same effects of preventing graying of the hair and restoring grayed hair to its natural color were observed.

EXAMPLE 9

Milky lotions (ML-I to ML-III) for hair were prepared by separately dissolving components 1 to 5 and components 6 to 10 listed in Table XV while heating them to 80° C., admixing and emulsifying these two solutions, adding component 11 during cooling the resultant emulsion with uniformly stirring.

TABLE XV

| Component | Present Invention I | Invention II | Comp. Ex. III |
|---|---|---|---|
| 1 Lanolin alcohol | 5.0 | 5.0 | 5.0 |
| 2 Isopropyl palmitate | 2.0 | 2.0 | 2.0 |
| 3 Stearic acid | 5.0 | 5.0 | 5.0 |
| 4 Sorbitan monostearate | 1.0 | 1.0 | 1.0 |
| 5 Heptadecanoic acid | 1.5 | — | — |
| 6 Peptide I | 0.0005 | 0.0005 | — |
| 7 Triethanolamine | 1.0 | 1.0 | 1.0 |
| 8 Propylene glycol | 5.0 | 5.0 | 5.0 |
| 9 Methyl p-hydroxybenzoate | small amount | small amount | small amount |
| 10 Purified water | balance | balance | balance |
| 11 Perfume | small amount | small amount | small amount |

Likewise, the effects of preventing graying of the hair and restoring grayed hair to its natural color were examined in the same manner as in Example 2. The results obtained are summarized in Table XVI and XVII below.

TABLE XVI

| This Inv. (ML-II) is better | This Inv. (ML-II) is somewhat better | Same | Comp. Ex. (ML-III) is somewhat better | Comp. Ex. (ML-III) is better |
|---|---|---|---|---|
| 6 | 9 | 5 | 0 | 0 |

TABLE XVII

| This Inv. (ML-I) is better | This Inv. (ML-I) is somewhat better | Same | This Inv. (ML-II) is somewhat better | This Inv. (ML-II) is better |
|---|---|---|---|---|
| 3 | 8 | 6 | 3 | 0 |

The results listed in Tables XVI and XVII demonstrate that the milky lotion (ML-II) of the present invention including peptide I makes it possible to lower the grayed hair rate and exhibits remarkable effect of preventing graying of the hair and restoring grayed hair to its natural color compared with the comparative milky lotion (ML-III) and that the milky lotion of the invention (ML-I) containing both peptide I and heptadecanoic acid exhibits such effect more excellent than that of the milky lotion (ML-II).

In addition, during and after the application of the milky lotions of the present invention for 3 months, no abnormality was observed in the condition of the scalp.

EXAMPLE 10

Milky lotions were prepared in the same manner as in Example 9 except for using, instead of peptide I, peptide II, (Nle$^4$)-alpha-MSH or (D-Phe$^7$)-alpha-MSH and the properties thereof were examined. The same effects of preventing graying of the hair and restoring grayed hair to its natural color as in Example 9 were obtained.

EXAMPLE 11

Hair tonics (HT-I to HT-III) were prepared in the same manner as in Example 5 except that human beta-MSH was substituted for alpha-MSH used in Example 5 and properties of the resultant hair tonics were examined. The results obtained are summarized in Tables XVIII and XIX.

TABLE XVIII

| This Inv. (HT-II) is better | This Inv. (HT-II) is somewhat better | Same | Comp. Ex. (HT-III) is somewhat better | Comp. Ex. (HT-III) is better |
|---|---|---|---|---|
| 1 | 10 | 9 | 0 | 0 |

TABLE XIX

| This Inv. (HT-I) is better | This Inv. (HT-I) is somewhat better | Same | This Inv. (HT-II) is somewhat better | This Inv. (HT-II) is better |
|---|---|---|---|---|
| 3 | 8 | 5 | 4 | 0 |

The results listed in Tables XVIII and XIX demonstrate that the hair tonic (HT-II) of the present invention including human beta-MSH makes it possible to lower the grayed hair rate and exhibits remarkable effect of preventing graying of the hair and restoring grayed hair to its natural color compared with the comparative hair tonic (HT-III) and that the hair tonic of the invention (HT-I) containing both human beta-MSH and glyceryl monopentadecanoate exhibits such effect more excellent than that of the hair tonic (HT-II).

What is claimed is:

1. A method for preventing graying of the hair or restoring grayed hair to its natural color, said method comprising applying to the scalp a sufficient amount of a solution comprising an effective amount of (A) at least one compound selected from the group consisting of forskolin and derivatives thereof.

2. The method according to claim 1 wherein the forskolin and derivatives thereof are selected from the group consisting of compounds represented by the following general formula (II):

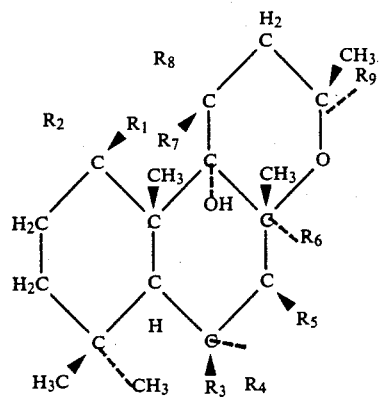

wherein $R_1$ to $R_8$ each represents a hydrogen atom, an oxygen atom, a hydroxy group, an amino group, an -O-acyl group having 1 to 25 carbon atoms, an acyl group having 1 to 25 carbon atoms, an -O-alkyl group having 1 to 25 carbon atoms, an -O-alkyl group having 1 to 25 carbon atoms, an alkyl group having 1 to 25 carbon atoms, a diethylaminomethyl group or a toluenesulfonyl group, provided that if they are oxygen atoms, they form double bonds together with the carbon atoms to which they are bonded; and $R_9$ represents a hydrogen atom, an alkenyl group having 2 to 25 carbon atoms, an alkyl group having 1 to 25 carbon atoms, a dialkylaminohydroxyethyl group having 1 to 25 carbon atoms, an aldehyde group or an epoxy group.

3. The method according to claim 1 wherein the compound (A) is a crude extract obtained from roots of Coleus forskohlii containing forskolin related compounds, a compound obtained by further separating and purifying the crude extract, a compound synthesized from intermediates thereof or derivatives thereof obtained by a synthetic method or any combination thereof.

4. The method according to claim 1 wherein the forskolin and derivatives thereof are selected from the group consisting of forskolin, 14,15-dihydroforskolin, 11-beta-hydroxylforskolin, 1-6-diacetylforskolin, 7-deacetylforskolin, 6-acetyl-deacetylforskolin, 7-succinyl-7-deactylforskolin, 7-butyryl-7-deacetylforskolin, 7-toluenesulfonyl-7-deacetylforskolin, 6-hexanoylforskolin, 1-diethylaminomethyl-6-acetyl-7-deacetylforskolin, forskolin 1,9-carbonate, forskolin 1,9-sulfonate, forskolin 6,7-carbonate and forskolin 1,9; 6,7-dicarbonate.

5. The method according to claim 1 wherein the amount of the compound (A) ranges from 0.000001 to 10% by weight.

6. The method according to claim 1 wherein the amount of the compound (A) ranges from 0.01 to 5% by weight.

* * * * *